United States Patent [19]

Ross

[11] Patent Number: 4,600,387
[45] Date of Patent: Jul. 15, 1986

[54] RUBBER DAM FRAME FOR DENTAL WORK

[76] Inventor: Robert A. Ross, 2117 Jackson Heights Dr., Sebring, Fla. 33870

[21] Appl. No.: 616,568

[22] Filed: Jun. 4, 1984

[51] Int. Cl.[4] .............................................. A61C 5/14
[52] U.S. Cl. .................................................... 433/136
[58] Field of Search .............................. 433/136, 137

[56] References Cited

U.S. PATENT DOCUMENTS

| | | | |
|---|---|---|---|
| 1,774,285 | 8/1930 | Middaugh | 433/137 |
| 2,937,445 | 5/1960 | Erickson | 433/93 |
| 3,396,468 | 8/1968 | Dayhoff | 433/93 |
| 4,544,357 | 10/1985 | Williams | 433/136 |

Primary Examiner—Robert Peshock
Attorney, Agent, or Firm—Duckworth, Allen, Dyer

[57] ABSTRACT

A dam frame and a dam assembly for use during dental procedures. A two-member elliptical radiolucent plastic frame is provided having arcuate openings matching the upper and lower teeth of a patient and an opening adjacent the throat area. A rubber dam sheet is disposed between the two frame members so as to cover the openings. To produce a dam assembly, the frame is bent along its minor axis to place in a patient's mouth. The dam sheet may be cut or punched to isolate one or more teeth with the uncut portions protecting the patient's throat and mouth.

14 Claims, 5 Drawing Figures

RUBBER DAM FRAME FOR DENTAL WORK

BACKGROUND OF THE INVENTION

1. Field of the Invention

The present invention relates generally to the use of rubber dams in dentistry, and more particularly to a rubber dam frame for holding a dam in place during dental procedures.

2. Description of the Prior Art The use of rubber dams during various dental procedures has been known for many years. Generally, a dam comprises a thin rubber sheet or the like which is stretched in place over a frame held against the patient's face. If a particular tooth is to be worked on, a hole is cut in the dam and pushed down over the tooth with a clamp applied to hold the dam in place. As may now be understood, the dam isolates the tooth to prevent the patient from swallowing or aspirating foreign objects. The dam also functions to keep the field aseptic. Greater difficulty is experienced in the use of a dam when all of the teeth are to be isolated since awkward and uncomfortable clamps are necessary. Furthermore, the prior art dam holders restrict access to the teeth not being operated on such that in some instances the dam frame must be removed when taking X-rays or checking bite and the like, and in other cases, the dam and clamp interferes with an accurate picture.

A rubber dam holder is described by Kahn in U.S. Pat. No. 4,204,329 using a single U-shaped frame having barbs for holding a rubber dam. The holder is placed over the patient's face with the novelty of the invention involving a hinge positioned in the individually pivot toward the other to provide access to the interior of the patient's mouth as for taking X rays. Swan-Gett et al in U.S. Pat. No. 3,772,790 disclose a tooth-isolating shield having an apron of deformable material and semi-rigid dentitian bridge conforming members. Although this patent discloses an improvement over the sheet rubber dam arrangement, it must be tailored to conform to the individual patient's mouth. Daigle, U.S. Pat. No. 2,680,908, shows a dental isolator cone which must be retained in the mouth by the biting action of opposed teeth on a surface thereof. None of these known prior art dams or shields fill the need for a low-cost, disposable dental dam which is comfortable to the patient and provides the dentist with access to the interior of the patient's mouth for X-rays and the like.

SUMMARY OF THE INVENTION

The present invention is a rubber dam frame having two parts; an upper member and a complementary lower member. Each member is formed from a pliable plastic material, preferably, and is generally elliptically shaped to match the normal curvature and contour of the human teeth and gums. Each frame member consists of an outer rim and inner rim. The inner and outer rims are disposed to form a space therebetween to permit placement over the teeth and gums of the patient. The inner and outer frames are connected together at the center by narrow webs which, as will be discussed more fully herein below, function as a hinge. The upper frame members includes a tongue projecting from one surface thereof and the lower frame member includes a complementary groove into which the tongue can snap. As will be understood, the upper and lower members are identical except for the tongue and groove construction. To utilize the frame in accordance with the invention, the lower member is placed on a firm surface. A rubber dam sheet is placed over the lower member and the upper member then aligned with the lower member on top of the dam. The upper member is then pressed downward such that the tongue portion of the member and the rubber sheet material snaps into the grooves of the lower member. Thus, the rubber dam is captivated between the two frame members.

The excess rubber dam material is cut away around the periphery of the joined frames, and the dam and dam holder are then ready for use. If the dentist wishes to isolate one tooth, he may make a small cut or punch an opening in the web of dam material at the location of the tooth before the dam is inserted into the patient's mouth. If all of the teeth are to be isolated, either upper or lower, the rubber sheet is split along the line of teeth. After the dam is cut for the particular application, the frames may be then partially folded together along a center hinge line. Through the use of a suitable plastic, a slight restoring force will tend to open the partially folded dam. The frame is placed in the patient's mouth and pressed down over the upper and lower teeth toward the gums. Where a slot has been cut for an entire line of teeth, the frame portions are forced downward below the gum line such that the teeth project through the slot. Similarly, if a single tooth is to be isolated, the opening for that tooth is pushed down around the tooth and a suitable clamp placed on the tooth to hold the dam in place.

As will now be apparent, only the specific tooth or teeth upon which the dentist will operate are exposed. The other teeth are covered or protected by the rubber dam material between the inner and outer frame borders, and the space over the throat is covered. If the dentist should accidentally drop a root canal instrument, crown, inlay, broken tool, or similar foreign object, the dam will eliminate the dangerous risk of injury to the patient from swallowing or aspirating such objects. Impressions can be made with no danger of the impression material flowing down the throat and gagging the patient.

Preferably, the plastic material of the frame is radioluscent plastic; and therefore, X-rays may be taken with the dam in place. The frame assists in holding X-ray film placed between the frame and the gingiva. Although the rubber dam frame of the invention is very low cost and may be disposed of after use, a dam made to fit a particular patient may be washed, sterilized, and placed in the patient's folder for a subsequent appointment.

It is therefore a principal object of the invention to provide a low-cost, effective frame for a rubber dam for use in dental procedures.

It is another object to provide a convenient dental dam which is comfortable to the patient and which may be used to isolate a single tooth or a number of teeth.

It is still another object of the invention to provide a rubber dam frame which will prevent the patient from swallowing or aspirating foreign objects.

It is yet another object of the invention to provide a frame for a rubber dam which, when in use, is intraoral and permits the dentist to have access to the interior of the mouth for X-rays and the like.

These and other objects and advantages of the invention will become apparent from the following detailed description when read in conjunction with the drawings.

DETAILED DESCRIPTION OF THE PREFERRED EMBODIMENT

Figure 1:
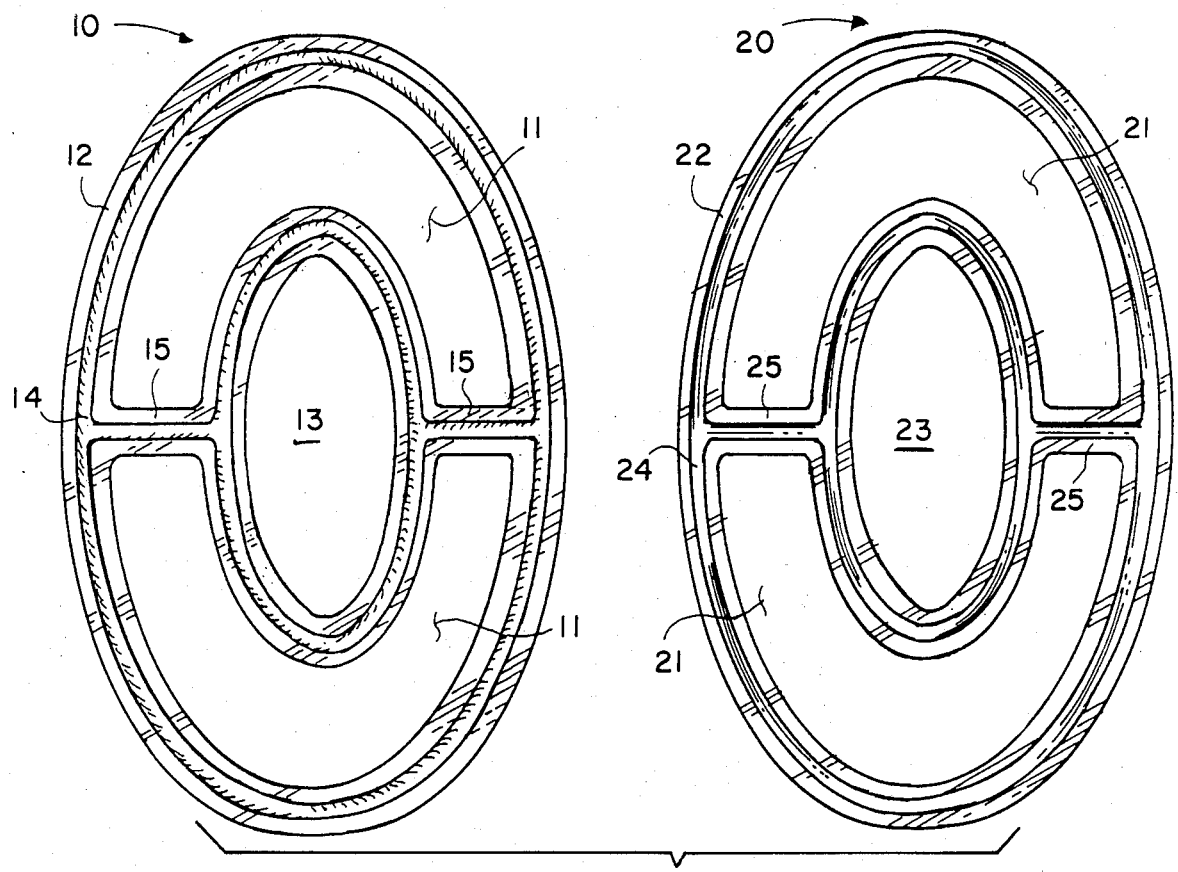
FIG. 1 shows a plan view of the upper and lower frame members of the invention.

Referring first to FIG. 1, the two members of a frame 5 in accordance with the present invention are shown. The frame member shown generally at 10 will be referred to as the upper member and the frame member shown generally at 20 will be called the lower member. Upper member 10 comprises a body portion 12 having a projecting tongue portion 14 attached thereto. Body portion 12 has a general configuration of two ellipses joined along their minor axes by a cross-member 15 thereby forming two spaces 11 which generally will conform to the gum contours of a patient. It is contemplated that the frames of the invention will be manufactured in various sizes and proportions to fit a variety of patients. Members 10 and 20 are preferably molded from a resilient, flexible plastic which is radiolucent.

The inner ellipse defines a space 13 which, as will be noted below, will be over the patients throat area when the frame is in use.

Lower frame member 20 is complementary to upper frame member 10 in its shape. However, body portion 22 of frame 20 is slightly thicker than body portion 12 of the upper frame and includes a groove 24 complementary to tongue 14.

Figure 2:
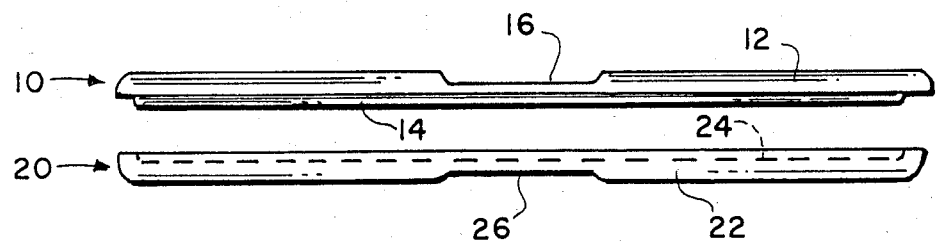
FIG. 2 is an edge view of the upper and lower frame members of FIG. 1.

As will be noted in FIG. 2, the outer portion of frame member 10 includes a relieved area 16 along cross members 15 while frame 20 includes a relieved area 26 along cross members 25. Relieved areas 16 and 26 thereby form a self-hinge to permit folding of the frame as discussed hereinbelow.

Figure 3:
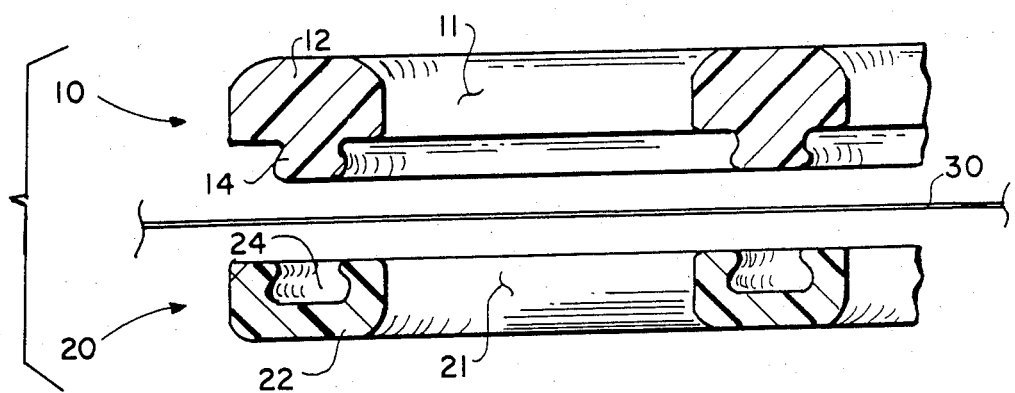
FIG. 3 is an enlarged cross-sectional view of a portion of the upper and lower frame members of FIG. 1 disposed in position for snapping together with a rubber dam sheet disposed therebetween.
Figure 4:
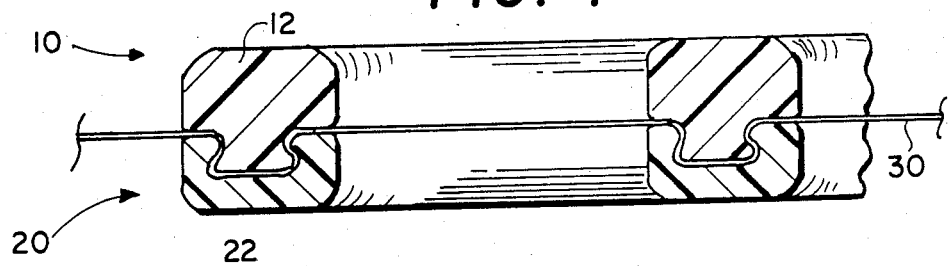
FIG. 4 is the arrangement of FIG. 3 showing the upper frame member having been snapped into place in the lower frame member to hold the rubber dam in place.

Turning now to FIGS. 3 and 4, the tongue and groove construction of frame members 10 and 20 is more clearly shown. As will be seen, tongue 14 of upper member 10 is complementary to groove 24 in lower member 20. By virtue of the flexibility of the plastic from which members 10 and 20 are formed, tongue 14 may be snapped into groove 24. A rubber dam sheet 30 is indicated in FIG. 3 disposed between member 10 and member 20 preparatory to joining members 10 and 20 together. By placing lower member 20 on a firm surface and pressing upper member 10 downward, tongue 14 will force dam sheet 30 into groove 24 with tongue 14 snapping into place as seen in the cross-sectional view of FIG. 4. As may now be understood, members 10 and 20 form a unitary frame 5.

Figure 5:
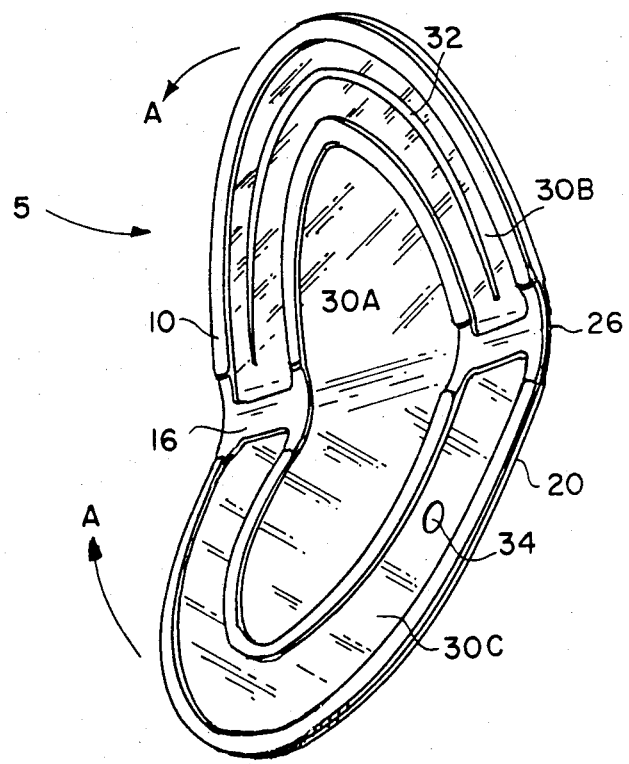
FIG. 5 is a perspective view of a set of frame members of the invention having a rubber dam installed therebetween, with the dam cut for isolating a single tooth in the lower member and cut for isolating all of the teeth in the upper member with the frame bent preparatory to inserting in the patient's mouth.

The excess rubber is then trimmed around the outer edges of frame 5. A typical frame ready for use is shown in FIG. 5. As will be noted, rubber dam sheet 30 forms three areas in frame 5. Area 30B will form a dam for the upper teeth of the patient, area 30C will form a dam for the lower teeth and area 30A will protect the patient's throat area. For the example of FIG. 5, upper dam area 30B has been cut to form a slot 32 to expose all of the patient's upper teeth while lower dam area 30C has had one small opening 34 punched therein to expose a single lower tooth.

To install frame 5 in the patient's mouth, the upper and lower portions are folded toward each other as indicated by arrows A causing the relieved portions 16, 26 of upper frame 10 and lower frame 20 to act as a hinge. The frame is then inserted into the patient's mouth and allowed to spring open. The slot 32, which will be aligned with the patient's upper teeth line, will permit frame 5 to be pushed between the gingiva and the patient's cheeks securely holding the frame 5 in place. Similarly, the portion of frame 5 contacting the patient's lower teeth may be pushed downward, forcing the selected tooth through opening 34. A clamp may then be applied to that tooth to hold the dam in place around it.

Advantageously, the entire frame 5 fits into the patient's mouth and the usual disadvantages of an external dam frame are eliminated. Saliva may be easily removed. Periapical film may be placed between the teeth and the lingual part of frame and are held in place by the edges of frame 5 without removal of the dam from the patient's mouth. As will be understood, the dam frame of the invention permits the use of a dam which is comfortable to the patient and provides maximum access for the dentist to the patient's mouth. Where necessary and desired, cuts in the dam may be made to permit the patient to close his mouth to check for bite without necessity of removing the dam.

Although a specific design for the frame members of the invention has been disclosed, it will be apparent to those of skill in the art that other means are equally suitable for joining the upper and lower frame members together. For example, pins and sockets may be used in place of a continuous tongue and groove arrangement. This modification and others are considered to fall within the spirit and scope of the invention.

I claim:

1. A frame for a rubber dental dam sheet comprising:
a first frame member having a first essentially elliptical outer rim portion and a first essentially elliptical inner rim portion, said inner and outer rim portions joined along the minor axes thereof by a pair of first cross members, said first frame member including a projecting tongue essentially coincident with said first inner and outer rim portions;
a second frame member having a second essentially elliptical outer rim portion and a second essentially elliptical inner rim portion, said second outer and inner rim portions essentially matching said first outer and inner rim portions, said second inner and outer rim portions joined along the minor axes thereof by a pair of second cross members, said second frame member including a groove complementary to said tongue and essentially coincident with said second inner and outer rim portions; and
said first frame member adapted thereby to have said tongue snapped into said groove of said second frame member for captivating a rubber dam sheet therebetween.

2. The frame as defined in claim 1 in which said first and second frame members are formed of a flexible plastic.

3. The frame as defined in claim 2 in which said plastic is radioluscent.

4. The frame as defined in claim 1 in which said pairs of first and second cross members are relieved to thereby function as self-hinges for permitting said frame to hinge along said minor axes.

5. A dam assembly for use in dental procedures comprising:
an essential elliptical frame formed of two independent interconnected frame portions, said frame portions foldable along the minor axis thereof, the size of said frame selected to permit insertion in a dental patient's mouth to thereby overlay the patient's upper and lower teeth;
said frame having a first arcuate space matching the upper teeth of said patient, and a second arcuate space matching the lower teeth of the patient, and an elliptical space adjacent the throat area of the patient; and
a flexible dental dam sheet locked between said frame portions and overlaying said first arcuate space, said second arcuate space, and said elliptical space.

6. The frame assembly as defined in claim 5 in which said frame is formed from a resilient plastic.

7. The frame assembly as defined in claim 6 in which said plastic is radioluscent.

8. A dam assembly for use in dental procedures comprising:
an essentially elliptical frame formed of two independent interconnected frame portions, said frame portions foldable along the minor axis thereof, the size of said frame selected to permit insertion in a dental patient's mouth to thereby overlay the patient's upper and lower teeth;
said frame portions having a first arcuate space matching the upper teeth of said patient, and a second arcuate space matching the lower teeth of the patient, and an elliptical space adjacent the throat area of the patient;
a flexible dental dam sheet locked between said frame portions and overlaying said first arcuate space, said second arcuate space, and said elliptical space; and
said frame, including biasing means for urging said frame when folded and inserted in a dental patient's mouth, toward the patient's upper and lower teeth.

9. The frame assembly as defined in claim 8 in which said biasing means comprises said frame being formed from resilient plastic.

10. A dam assembly for use in dental procedures comprising:
a first frame portion formed of a resilient material;
a second frame portion formed of a resilient material and dimensioned as first frame portion, said second frame portion opposing said first frame portion;
a flexible dental dam sheet; and
means for releasably fitting said first and second frame portions together with said dam sheet therebetween, wherein said assembly may be inserted in a patient's mouth and said sheet fitted between said members may be selectively pierced to permit access to one or more of the patient's teeth.

11. The dam assembly recited in claim 10 further comprising means for bending said first and second frame means about a common hinge axis.

12. A dam assembly as recited in claim 11 wherein said releasable fitting means comprises a tongue on said first frame member and a groove on said second frame member.

13. A dam assembly as recited in claim 12 further comprising:
said first frame member having a pair of generally parallel tongues;
said second frame member having a pair of generally parallel grooves, each groove interconnecting with a corresponding tongue of said first frame member; and wherein
a portion of said dam sheet extends between each tongue-groove combination.

14. The dam assembly recited in claim 13 wherein said bending means comprises:
said tongues and grooves of said first and second frame members extending along only a portion of said first and second frame members;
a portion of said first and second frame members where said tongue and grooves are not located being relieved with a narrower dimension than the remainder of the respective one of said first and second frame members; and wherein
said portion of said first and second frame members without said tongue and groove and with said relief forms a flexible hinge between said first and second frame members.

* * * * *